US008651106B1

(12) United States Patent
Morgan, Jr.

(10) Patent No.: US 8,651,106 B1
(45) Date of Patent: Feb. 18, 2014

(54) INTERNAL NOSE FILTER MOUNTING DEVICE, METHOD, AND KIT

(71) Applicant: Toby S. Morgan, Jr., Rome, GA (US)

(72) Inventor: Toby S. Morgan, Jr., Rome, GA (US)

(73) Assignee: Toby S. Morgan, Jr., Rome, GA (US)

( * ) Notice: Subject to any disclaimer, the term of this patent is extended or adjusted under 35 U.S.C. 154(b) by 0 days.

(21) Appl. No.: 13/715,447

(22) Filed: Dec. 14, 2012

(51) Int. Cl.

| | |
|---|---|
| ***A61M 16/00*** | (2006.01) |
| ***A62B 23/00*** | (2006.01) |
| ***A62B 23/06*** | (2006.01) |

(52) U.S. Cl.
USPC ............ 128/206.11; 128/205.27; 128/205.28; 128/205.29

(58) Field of Classification Search
USPC ........... 128/205.27–205.29, 206.11; 606/201, 606/196, 204.45; 63/29.1, 29.2, 900, 63/14.1–14.5; 24/303, 66.1
See application file for complete search history.

(56) References Cited

U.S. PATENT DOCUMENTS

| | | | | |
|---|---|---|---|---|
| 142,477 | A * | 9/1873 | James | 128/206.11 |
| 3,034,320 | A * | 5/1962 | Feibelman | 63/14.1 |
| 4,105,035 | A | 8/1978 | Rella | |
| 5,850,834 | A * | 12/1998 | Yoshida et al. | 128/204.12 |
| 5,947,119 | A | 9/1999 | Reznick | |
| 6,213,121 | B1 * | 4/2001 | Cardarelli | 128/206.18 |
| 7,263,996 | B2 | 9/2007 | Yung Ho | |
| 7,318,438 | B2 | 1/2008 | Brown | |
| 2004/0147954 | A1 | 7/2004 | Wood | |
| 2007/0283963 | A1 * | 12/2007 | Sims | 128/206.18 |

* cited by examiner

*Primary Examiner* — Justine R Yu
*Assistant Examiner* — Michael Tsai
(74) *Attorney, Agent, or Firm* — Sutherland Asbill & Brennan LLP

(57) ABSTRACT

Internal nose filter mounting devices, methods and kits are provided. The nose filter mounting device includes first and second septum magnets, each septum magnet having two opposing faces and being configured to be inserted into a nostril of a user such that one face is adjacent the nasal septum therein and the first and second septum magnets may magnetically engage across the septum. The nose filter mounting device also includes first and second filter magnets connected to the first and second septum magnets, respectively, each filter magnet being configured to mate with filter elements in the nostrils of the user.

22 Claims, 3 Drawing Sheets

INTERNAL NOSE FILTER MOUNTING DEVICE, METHOD, AND KIT

TECHNICAL FIELD

The present invention relates generally to the field of filtration devices for nasal passages, and more particularly to internal magnetic nose filter mounting devices, kits, and methods for use thereof.

BACKGROUND

Global air contamination is worsening each year and an increased number of persons are suffering medical problems due to the inhalation of contaminants. For example, airborne contaminants may include the output from factories, combustion exhaust from vehicles, sand in desert climates, and chemicals and other toxins in workplaces. Additionally, many people suffer from allergies to pollens, dust, grasses, molds, and other airborne allergens.

The majority of inhaled air, including airborne allergens and contaminants, enters the body through the nose. Exposure to such contaminants may result in severe rhinitis, post-nasal drip, nasal polyps, nasal obstruction, sinusitis, asthma, bronchitis, COPD, and various other conditions that may necessitate treatments including antibiotics, antihistamines, nasal sprays, and oral and/or injected steroids. Allergy sufferers may require extensive allergy testing to determine the nature of their allergies. In some cases, medicinal treatments are not sufficient and surgery of the nose and/or sinuses is necessary to obtain relief for a patient.

Various nose filters are known that allow air to be filtered prior to inhalation through the nose and/or mouth. For example, devices such as face masks and adhesive filters that adhere to the outer surface of the nostrils allow air to be filtered prior to inhalation by a wearer. However, such filters experience problems such as user discomfort and irritation of the sensitive nasal tissues. Additionally, these filters are visible to others and are not aesthetically attractive. Furthermore, these filters may not be suitable for use in all situations.

Filtration devices that are worn within the nostrils of a user are also known. For example, U.S. Pat. No. 6,213,121 to Cardarelli discloses a surgically implantable nasal filtration device. The device relies on a complex design including three sleeves, two smaller and one large, that are punched through the septum. A pair of stabilizer plates distributes stresses and a large septum stud supports snap-on filter elements. However, the size and complex design of the device make it difficult to implant and remove, and possibly painful for wearers. For example, the device requires a large hole in the anterior/cartilaginous septum, which can result in severe discomfort and nasal bleeding, and cause whistling while breathing if the hole persists after removal of the device.

Accordingly, it would be desirable to provide devices and methods to improve the comfort and aesthetics of nasal filtration.

SUMMARY

Devices, methods, and kits for nasal filtration are provided. In one aspect, a nose filter mounting device is provided. The device includes a first septum magnet having a first magnet face and a second magnet face opposing the first magnet face, and configured to be inserted into a first nostril of a user such that the first magnet face is adjacent to the nasal septum therein. The device also includes a second septum magnet having a third magnet face and a fourth magnet face opposing the third magnet face, and being configured to be inserted into a second nostril of the user such that the third magnet face is adjacent to the nasal septum. The first and second septum magnets are configured to magnetically engage across the septum of the user. The device also includes first and second filter magnets connected to the first and second septum magnets, respectively. The first and second filter magnets are configured to mate with filter elements in the first and second nostrils of the user.

In another aspect, a method for implanting a nose filter mounting device is provided. The method includes inserting a first septum magnet into a first nostril of a user such that the a first magnet face of the first septum magnet is adjacent to the nasal septum therein, inserting a second septum magnet into a second nostril of the user such that a third magnet face of the second septum magnet is adjacent to the nasal septum and the first and second septum magnets are magnetically engaged across the septum of the user, and positioning the first and second septum magnets such that a first filter magnet connected to the first septum magnet and a second filter magnet connected to the second septum magnet are configured to mate with filter elements in the first and second nostrils of the user.

In yet another aspect, a kit is provided. The kit includes a first septum magnet having a first filter magnet connected thereto and being configured to be inserted into a first nostril of a user such that a first magnet face of the first septum magnet is adjacent to the nasal septum therein, a second septum magnet having a second filter magnet connected thereto and being configured to be inserted into a second nostril of the user such that a third magnet face of the second septum magnet is adjacent to the nasal septum, and one or more filter elements configured to mate with the first or second filter magnets.

DETAILED DESCRIPTION

The present application will now be described more fully hereinafter with reference to the accompanying drawings, in which several embodiments of the application are shown. Like numbers refer to like elements throughout the drawings.

Mounting Device

Figure 1:
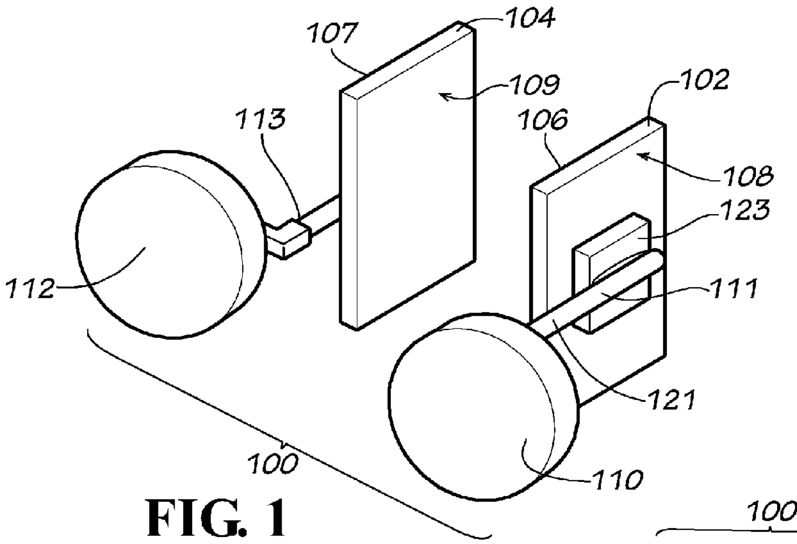
FIG. 1 is a perspective view of a nose filter mounting device in accordance with one or more embodiments of the present invention.
Figure 2:
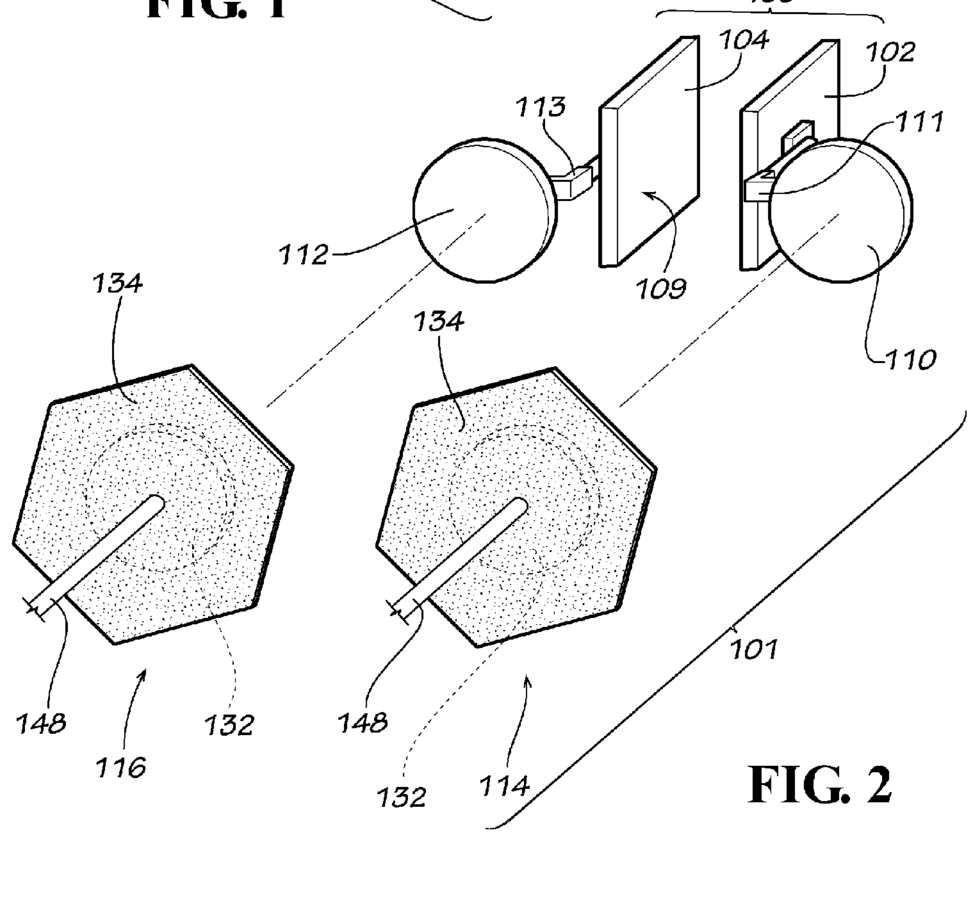
FIG. 2 is a perspective view of a nose filter mounting device and filter elements in accordance with one or more embodiments of the present invention.

In one aspect, as shown in FIG. 1, an internal nose filter mounting device 100 is provided. In one embodiment, the mounting device 100 includes two septum magnets 102, 104. The first septum magnet 102 has a first magnet face 106 and a second magnet face 108 opposing the first magnet face. The second septum magnet 104 has a third magnet face 109 and a fourth magnet face 107 opposing the third magnet face 109. A first filter magnet 110 is connected to the first septum magnet 102 and a second filter magnet 112 is connected to the second septum magnet 104. As shown in FIG. 2, the first and second filter magnets 110, 112 are configured to mate with filter elements 114, 116.

Figure 3A:
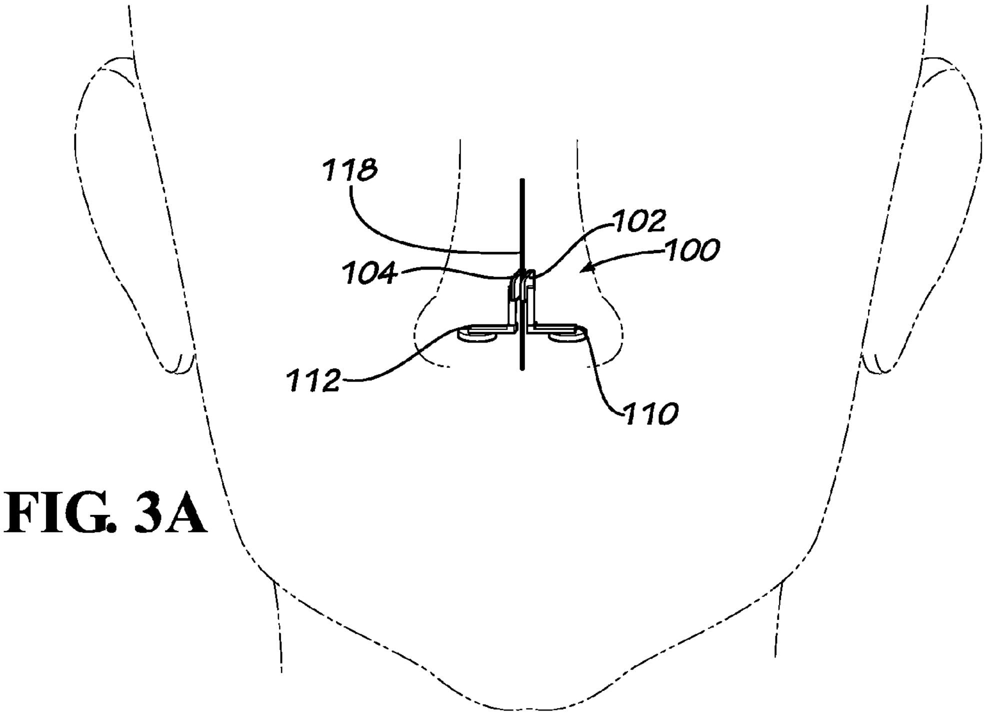
FIG. 3A is a perspective view of an implanted nose filter mounting device in accordance with one or more embodiments of the present invention.
Figure 3B:
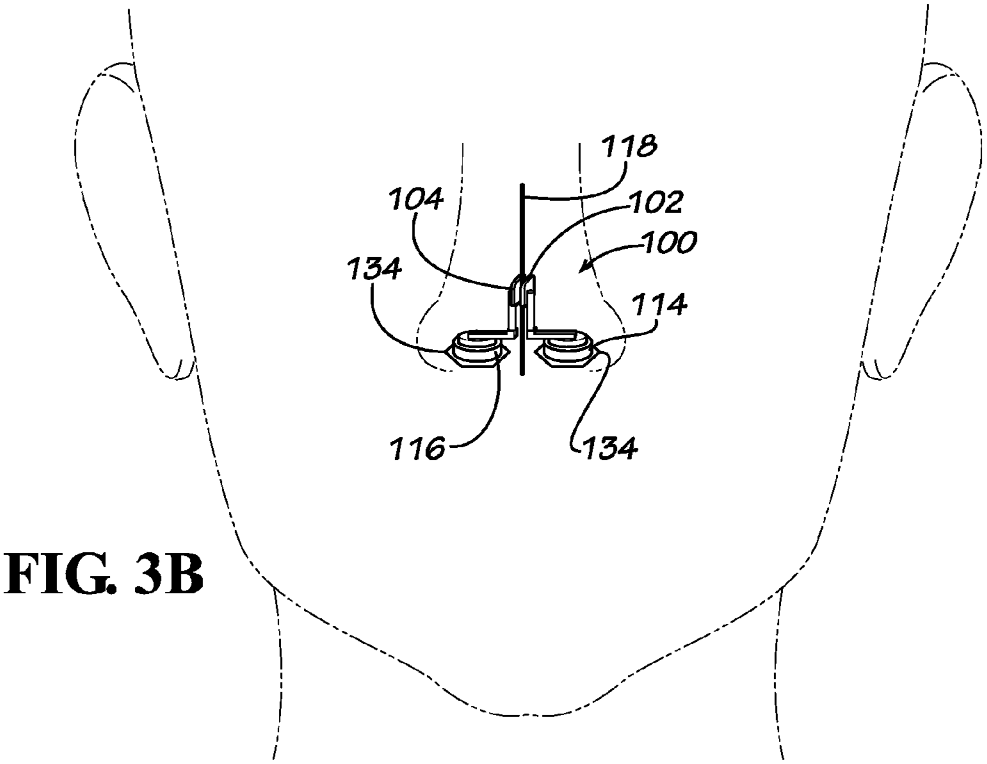
FIG. 3B is a perspective view of an implanted nose filter mounting device with mounted filter elements, in accordance with one or more embodiments of the present invention.

As shown in FIGS. 3A and 3B, the first septum magnet 102 is configured to be inserted into a first nostril of a user such that the first magnet face 106 is adjacent to the nasal septum 118. Likewise, the second septum magnet 104 is configured to be inserted into a second nostril of the user such that the third magnet face 109 is adjacent to the nasal septum 118. For example, when the device is implanted in the nasal cavity of a patient, the first and third magnet faces 106, 109 may be substantially parallel to the nasal septum and lie flat against it. The first and second septum magnets 102, 104 are configured to magnetically engage across the septum 118 of a user. Upon placement within the nostrils, the first and second filter magnets 110, 112 may mate with filter elements 114, 116 in the nostrils of a user, as shown in FIG. 3B.

The septum magnets may be sized and shaped to fit within the nasal passages of a patient. For example, the septum magnets may have a size and shape such that they may be inserted through the nostril opening of a user and positioned adjacent the nasal septum without causing trauma to the patient. In certain embodiments, the septum magnets have a width from about 3 mm to about 15 mm and a side length or diameter from about 3 mm to about 15 mm. For example, the septum magnets may have a width of about 7 mm.

The first and second septum magnets may have opposite polarities and magnetic strength to firmly hold the device in place within the nostrils. For example, the septum magnets may be strong enough to firmly fix the device adjacent the septum without compromising the blood supply to the mucosa or causing tissue loss. For example, the first and second septum magnets may be rare-earth magnets.

The magnet faces of the septum magnets may be polygonal, circular, rectangular, triangular, elliptical, or otherwise shaped to be positioned adjacent the septum within the nasal passage of a user. For example, as shown in FIG. 1, the magnet faces 108, 109 may be rectangular. In one embodiment, the magnet faces are rectangular and have a first side length from about 3 mm to about 15 mm and a second side length from about 3 mm to about 15 mm. For example, the magnet faces may be rectangular and have a first side length of about 7 mm and a second side length of about 7 mm. In another embodiment, the first, second, third, and fourth magnet faces are circular and have a diameter from about 3 mm to about 15 mm. For example, the magnet faces may be circular and have a diameter of about 7 mm.

In certain embodiments, as shown in FIG. 1, the first filter magnet 110 is connected to the second magnet face 108 of the first septum magnet 102 and the second filter magnet 112 is connected to the fourth magnet face 107 of the second septum magnet 104. For example, the filter magnets may be connected to the septum magnets by any suitable connecting means, including backing plates, posts, brackets, filaments, welds, adhesives, and combinations thereof. Such connecting means may be rigid or flexible in nature.

For example, as shown in FIG. 1, the first and second filter magnets 110, 112 may be connected to the first and second septum magnets 102, 104, respectively, via connecting means 111, 113 that position the first and second magnets within the nasal passages. In another embodiment, the first and second filter magnets are connected to the first and second septum magnets via flexible filaments that allow the first and second filter magnets to hang within the nasal passages. For example, the filter magnets may be connected to the septum magnets such that when the device is implanted in the nasal cavity of a patient, the filter magnets are facing the nostril openings.

In certain embodiments, the connecting means includes a post that extends from the septum magnet to the filter magnet. For example, the post may have a cross-sectional diameter from about 2 mm to about 10 mm and a length from about 2 mm to about 15 mm. In one embodiment, as shown in FIG. 1, the connecting means 111 includes a backing plate 123 adjacent to the second face 108 of the first septum magnet 102 and a post 121 attached thereto. The post 121 may be connected to the first filter magnet 110 such that the filter magnet 110 is distal from the septum magnet 102. Alternatively, the post may be connected to a backing plate adjacent to the non-magnet receiving face of the filter magnet. For example, the backing plates may be similarly sized and shaped as the septum or filter magnet to which they are attached, or the backing plates may be smaller than the magnets. The backing plates may be attached adjacent to the septum or filter magnets by an adhesive, weld, or other suitable connection. In certain embodiments, the septum and/or filter magnet backing plates have a width from about 3 mm to about 15 mm and a side length or diameter from about 3 mm to about 15 mm. For example, the backing plate may have a width of about 7 mm.

The connecting means may be fabricated from any combination of biocompatible materials known to those of skill in the art. For example, the components may be formed of metal, such as titanium, silver, stainless steel, nitinol, nickel, palladium, or gold, and/or a polymeric material, such as a silicone-based material. Alloys may be used such as cobalt chromium or synthetic materials such as hydroxylapatite. In certain embodiments, the connecting means is formed of one or more materials selected from the group consisting of titanium and gold. The connecting means may or may not be magnetic.

The filter magnets are connected to the septum magnets and are configured to mate with filter elements in the nostrils of the user. For example, the first and second filter magnets may be rare-earth magnets. As shown in FIG. 3A, the filter magnets 110, 112 may be positioned away from, and substantially perpendicular to, the septum magnets 102, 104 and facing toward the nostril openings when implanted in a user.

The magnet faces of the filter magnets may be polygonal, circular, rectangular, triangular, elliptical, or otherwise shaped to be positioned within the nostril of a user and receive filter elements. For example, as shown in FIG. 1, the faces of filter magnets 110, 112 may be circular. In one embodiment, the filter magnet faces are rectangular and have a first side length from about 3 mm to about 15 mm and a second side length from about 3 mm to about 15 mm. For example, the filter magnet faces may be rectangular and have a first side length of about 7 mm and a second side length of about 7 mm. In another embodiment, the filter magnet faces are circular and have a diameter from about 3 mm to about 15 mm. For example, the filter magnet faces may be circular and have a diameter of about 7 mm. In certain embodiments, the filter magnets have a width from about 3 mm to about 15 mm. For example, the filter magnets may have a width of about 7 mm.

Figure 5:
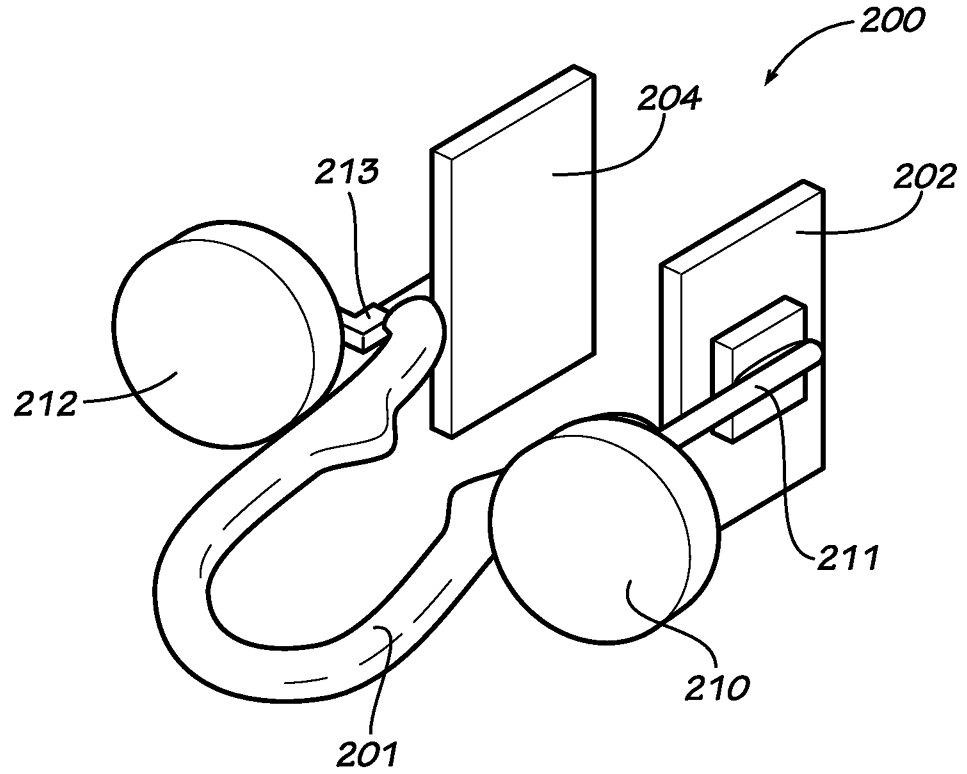
FIG. 5 is a perspective view of a nose filter mounting device in accordance with one or more embodiments of the present invention.

As shown in FIG. 5, in certain embodiments, the device 200 also includes a connecting member 201 connecting the first and second septum magnets 202, 204. For example, the connecting member 201 may be sized and shaped such that when the device 200 is mounted in the nostrils of the user, the connecting member 201 extends across the columella (i.e., the skin running from the tip of the nose to the upper lip and separating the nostrils) of the user. In certain embodiments, a first end of the connecting member 201 is attached at a location between the first septum magnet 202 and the first filter magnet 210, and a second end of the connecting member 201 is attached at a location between the second septum magnet 204 and the second filter magnet 212. For example, the connecting member 201 may be attached to the connecting means 211, 213.

The connecting member may allow easy insertion and removal of the device by the user. For example, the connecting member may be rigid or semi-flexible such that the connecting members holds the septum magnets in position and thereby reduces the amount of positioning required by the user. The connecting member may also help to secure the septum magnets within the nostrils, while preventing the septum magnets from moving too far into the nasal cavity.

Filters

In certain embodiments, as shown in FIG. 2, filter elements 114, 116 are provided to mate with the first and second filter magnets 110, 112 of the nose filter mounting device 100, in the nostrils of a user. Each filter element 114, 116 may include a ferromagnet 132 and a filter 134. As used herein, the term "ferromagnet" refers to materials which form permanent magnets or are attracted to magnets. For example, the ferromagnet may include a rare earth magnet. The design of the filter elements and mounting device advantageously allows a user to position a magnetic filter element in the range of, or near, the first or second filter magnet, without requiring the user to position or connect the filter manually. The opposing magnetic forces will orient the magnets into an aligned, or straight, configuration automatically.

The filter may be a flexible sheet material. The filter may be formed of one or more filter materials that are known to persons of skill in the art. For example, the filter may be formed of materials that are effective to filter allergens, pollutants, and/or irritants from the air, and allow a patient to breathe through their nostrils. The filter may be sized and shaped such that it creates a barrier within the nostril. For example, the filter may be circular or elliptical in shape. For example, the filter material may include a commercially available filter material that is non-latex, biocompatible, and 100% breathable. The filter may be designed to prevent up to 99% of airborne allergens including pollen, dust, bacteria, pet dander, molds, pollution, and other contaminants.

Figure 4:
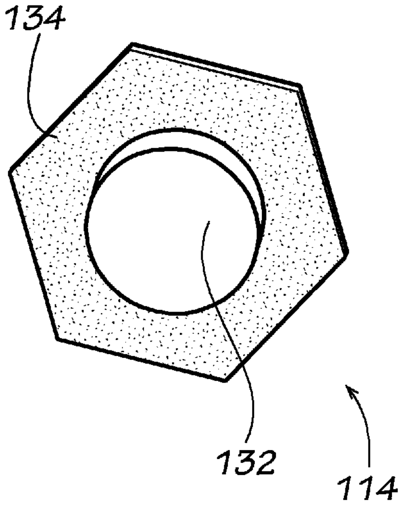
FIG. 4 is a perspective view of a filter element in accordance with one or more embodiments of the present invention.

In one embodiment of the filter elements, the ferromagnet and the filter are separate components. For example, the ferromagnet may be reusable while the filter is made for one-time use, e.g., designed to be changed on a daily basis or as frequently as is required by the quality of inhaled air. For example, the ferromagnet may be operable to secure a separate filter between the ferromagnet and the magnetic disc of a nose filter mounting device. In another embodiment of the filter elements, the ferromagnet 132 is integral with the filter 134. For example, the ferromagnet 132 may be provided in the center of a filter 134, as shown in FIG. 4.

In certain embodiments, as shown in FIG. 2, each filter element 114 has a filter filament 148 extending therefrom. For example, a filter filament may extend from the ferromagnet of a filter element such that when the filter element mates with the first or second magnet of a nose filter device, the filter filament is positioned near the nostril opening. For example, the filament may allow a user to easily remove the filter element by pulling on the filament. The filter filament may be formed of a flexible material, such as a biocompatible silicone-based material. The filter filament may include one or more protuberances that enable gripping by a user. For example, the protuberances may include a knob or tab.

Method

In another aspect, a method for implanting a nose filter mounting device is provided. The nose filter mounting device may be any device as described herein. The method includes inserting the first septum magnet into a nostril of the user such that the first magnet face is adjacent the nasal septum, inserting the second septum magnet into the second nostril of the user such that the third magnet face is adjacent the nasal septum and the first and second septum magnets are magnetically engaged across the septum, and positioning the first and second septum magnets such that the first filter magnet connected to the first septum magnet and the second filter magnet connected to the second septum magnet are configured to mate with filter elements in the nostrils. For example, a physician may both insert and position the device within the nostrils of a patient.

In certain embodiments, inserting the septum magnets into the nostrils may occur simultaneously. For example, devices including a connecting member may be inserted into the nostrils as a whole. In other embodiments, one septum magnet may be inserted prior to insertion of the second septum magnet. The septum magnets may be positioned upon insertion such that the filter magnets are configured to mate with filter elements in the nostrils of the user. For example, the user may position the filter magnets such that they are facing toward the nostril openings.

In certain embodiments, the method also includes mating one or more filter elements with the first and/or second filter magnets. The one or more filter elements may be any filter elements as described herein. For example, the one or more filter elements may each include a ferromagnet and a filter.

This method advantageously may require no anesthesia for initial device implantation. Additionally, this method produces no holes in the patient's septum. Furthermore, the device is easily implantable, positionable, and removable by a user. For example, to remove the device, a user or physician may disengage the magnetic connection between the septum magnets. Or, in device embodiments such as shown in FIG. 5, one may simply pull on the connecting member 201 for extraction or removal of the device.

Kit

In a third aspect, a kit is provided. In one embodiment, as shown in FIG. 2, the kit 101 includes a first septum magnet 102 having a first filter magnet 110 connected thereto, a second septum magnet 104 having a second filter magnet 112 connected thereto, and one or more filter elements 114, 116 configured to mate with the first or second filter magnets 110, 112. The first septum magnet 102 is configured to be inserted into a first nostril of the user such that the first magnet face 106 is adjacent to the nasal septum and the second septum magnet 104 is configured to be inserted into the second nostril of the user such that a third magnet face 109 is adjacent to the nasal septum.

The kit may include any combination of the first and second septum magnets, connecting means, filter magnets, and filter elements described herein.

Publications cited herein and the materials for which they are cited are specifically incorporated by reference herein. Modifications and variations of the methods and compositions described herein will be obvious to those skilled in the art from the foregoing detailed description. Such modifications and variations are intended to come within the scope of the appended claims.

I claim:

1. A nose filter mounting device comprising:

a first septum magnet having a first magnet face and a second magnet face opposing the first magnet face, the first septum magnet being configured to be inserted into a first nostril of a user such that the first magnet face is adjacent to a nasal septum therein;

a second septum magnet having a third magnet face and a fourth magnet face opposing the third magnet face, the second septum magnet being configured to be inserted into a second nostril of the user such that the third magnet face is adjacent to the nasal septum;

a first filter magnet connected to the first septum magnet; and a second filter magnet connected to the second septum magnet;

wherein the first and second septum magnets are configured to magnetically engage across the septum of the user, wherein the first and second filter magnets are configured to mate with filter elements in the first and second nostrils of the user.

2. The device of claim 1, wherein the first filter magnet is connected to the second magnet face and the second filter magnet is connected to the fourth magnet face.

3. The device of claim 1, wherein the first and second filter magnets are connected to the first and second septum magnets via brackets.

4. The device of claim 1, wherein the first, second, third, and fourth magnet faces are circular and have a diameter from about 3 mm to about 15 mm.

5. The device of claim 1, wherein the first, second, third, and fourth magnet faces are rectangular and have a first side length from about 3 mm to about 15 mm and a second side length from about 3 mm to about 15 mm.

6. The device of claim 1, further comprising a connecting member connecting the first and second septum magnets.

7. The device of claim 6, wherein the connecting member is sized and shaped such that the connecting member is adapted to extend across a columella of the user when the device is mounted in the nostrils of the user.

8. The device of claim 6, wherein a first end of the connecting member is attached at a location between the first septum magnet and the first filter magnet, and a second end of the connecting member is attached at a location between the second septum magnet and the second filter magnet.

9. The device of claim 1, wherein each filter element comprises:

a ferromagnet; and a filter.

10. A method for implanting a nose filter mounting device comprising:

inserting a first septum magnet into a first nostril of a user such that a first magnet face of the first septum magnet is adjacent a nasal septum therein;

inserting a second septum magnet into a second nostril of the user such that a third magnet face of the second septum magnet is adjacent the nasal septum and the first and second septum magnets are magnetically engaged across the septum of the user; and positioning the first and second septum magnets such that a first filter magnet connected to the first septum magnet and a second filter magnet connected to the second septum magnet are configured to mate with filter elements in the first and second nostrils of the user.

11. The method of claim 10, wherein the first filter magnet is connected to a second magnet face opposing the first magnet face, and the second filter magnet is connected to a fourth magnet face opposing the third magnet face.

12. The method of claim 10, further comprising mating one or more filter elements with the first and/or second filter magnets.

13. The method of claim 12, wherein the one or more filter elements each comprise:

a ferromagnet; and a filter.

14. A kit comprising:

a first septum magnet having a first filter magnet connected thereto, the first septum magnet being configured to be inserted into a first nostril of a user such that a first magnet face of the first septum magnet is adjacent a nasal septum therein;

a second septum magnet having a second filter magnet connected thereto, the second septum magnet being configured to be inserted into a second nostril of the user such that a third magnet face of the second septum magnet is adjacent the nasal septum; and one or more filter elements configured to mate with the first or second filter magnets.

15. The kit of claim 14, wherein the one or more filter elements each comprise:

a ferromagnet; and a filter.

16. The kit of claim 15, wherein the filter comprises a flexible sheet material that is breathable and capable of filtering pollutants and contaminants.

17. The kit of claim 15, wherein the ferromagnet and the filter are separate, the ferromagnet being reusable.

18. The kit of claim 15, wherein the ferromagnet is integral with the filter.

19. The kit of claim 14, wherein each filter element has a filament extending therefrom.

20. The kit of claim 19, wherein the filament comprises one or more protuberances.

21. The kit of claim 14, wherein the first and second filter magnets comprise rare-earth magnets.

22. The kit of claim 14, wherein the first and second septum magnets comprise rare-earth magnets.

* * * * *